(12) United States Patent
Verma et al.

(10) Patent No.: US 11,378,484 B2
(45) Date of Patent: Jul. 5, 2022

(54) END OF SERVICE LIFE DETERMINATION FOR PERSONAL PROTECTIVE EQUIPMENT

(71) Applicant: HONEYWELL INTERNATIONAL INC., Morris Plains, NJ (US)

(72) Inventors: Prashant Verma, Morris Plains, NJ (US); Raj Kamal Prasad, Morris Plains, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 476 days.

(21) Appl. No.: 16/471,455

(22) PCT Filed: Dec. 21, 2016

(86) PCT No.: PCT/US2016/067923
§ 371 (c)(1),
(2) Date: Jun. 19, 2019

(87) PCT Pub. No.: WO2018/118033
PCT Pub. Date: Jun. 28, 2018

(65) Prior Publication Data
US 2020/0225189 A1   Jul. 16, 2020

(51) Int. Cl.
*G01M 5/00* (2006.01)
*G01N 27/82* (2006.01)
(Continued)

(52) U.S. Cl.
CPC .......... *G01M 5/0033* (2013.01); *A41D 1/002* (2013.01); *A41D 13/0002* (2013.01);
(Continued)

(58) Field of Classification Search
CPC .. G01M 5/0033; G01M 5/005; G01M 5/0091; A41D 1/002; A41D 13/0002; A41D 19/0027; A62B 17/006; G01N 17/002; G01N 27/82; G01N 33/00; G01N 2033/0086; G01N 2291/02863; G01R 33/12; A42B 3/067
(Continued)

(56) References Cited

U.S. PATENT DOCUMENTS 9,911,292 B1 * 3/2018 Khoshkava .............. G08B 6/00
2007/0003761 A1   1/2007 Miyazono et al.
(Continued)

OTHER PUBLICATIONS

Annex to the communication dated Oct. 30, 2020 for EP Application No. 16828830.6, 2 pages.
(Continued)

*Primary Examiner* — Christopher P McAndrew
(74) *Attorney, Agent, or Firm* — Alston & Bird LLP

(57) ABSTRACT

Embodiments generally relate to personal protective equipment (PPE) (such as gloves, shoes/boots, hoods, protective clothing, etc.) for industrial applications. More specifically, the invention relates to using magnetic particles (e.g. incorporated within or attached/affixed to the PPE) so that a magnetic scan may be run to determine a change (e.g. decrease) in initial magnetic field signature (MFS) for the PPE). The change in MFS is used to determine end of service life of the PPE (such that the protective equipment should be retired or repaired).

19 Claims, 5 Drawing Sheets

(51) Int. Cl.
| | |
|---|---|
| *G01N 33/00* | (2006.01) |
| *G01N 17/00* | (2006.01) |
| *G01R 33/12* | (2006.01) |
| *A41D 1/00* | (2018.01) |
| *A41D 13/00* | (2006.01) |
| *A41D 19/00* | (2006.01) |
| *A62B 17/00* | (2006.01) |

(52) U.S. Cl.
CPC ........ *A41D 19/0027* (2013.01); *A62B 17/006* (2013.01); *G01M 5/005* (2013.01); *G01M 5/0091* (2013.01); *G01N 17/002* (2013.01); *G01N 27/82* (2013.01); *G01N 33/00* (2013.01); *G01R 33/12* (2013.01); *G01N 2033/0086* (2013.01); *G01N 2291/02863* (2013.01)

(58) Field of Classification Search
USPC .......................................................... 324/216
See application file for complete search history.

(56) References Cited

U.S. PATENT DOCUMENTS

| | | | |
|---|---|---|---|
| 2012/0146784 A1* | 6/2012 | Hines .................... | A42B 3/046 2/2.5 |
| 2015/0132574 A1 | 5/2015 | Aldridge et al. | |
| 2016/0044841 A1* | 2/2016 | Chamberlain ....... | A61N 1/3718 174/350 |

OTHER PUBLICATIONS

Decision to grant a European patent dated May 7, 2021 for EP Application No. 16828830.6, 2 pages.
International Search Report and Written Opinion for Application No. PCT/US2016/067923, dated Sep. 11, 2017, 12 pages.
Communication about intention to grant a European patent dated Dec. 23, 2020 for EP Application No. 16828830.6, 5 pages.

* cited by examiner

END OF SERVICE LIFE DETERMINATION FOR PERSONAL PROTECTIVE EQUIPMENT

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments generally relate to end of service life determination (ESLD) for personal protective equipment (PPE), for example PPE providing a protective barrier operable to shield a user from a hazard.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
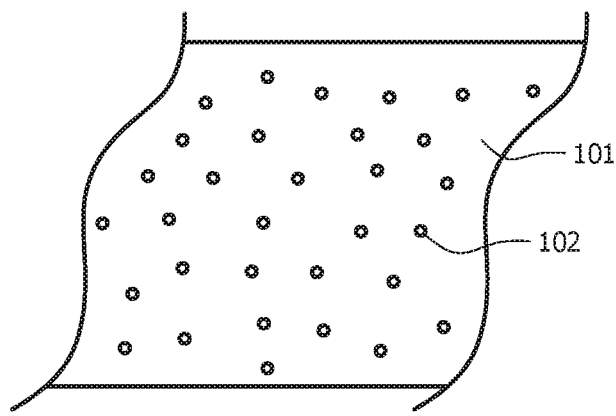
FIG. 1 illustrates a cross-sectional view of an exemplary embodiment of a personal protective equipment (PPE) matrix comprising magnetic particles distributed substantially homogeneously across the PPE.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The embodiments of this disclosure typically relate to end of service life determination (ESLD) of personal protective equipment (PPE), and, more specifically, relate to a way of determining via a magnetic scan when the PPE is still effective and when the PPE may have so much wear that it may no longer effectively protect the worker from the hazard that the PPE relates to (for example, from exposure to industrial chemicals). In other words, the magnetic scan may detect weak points in the PPE protective barrier (for example gloves, pants, hood, boot/shoe, etc. or other protective clothing/attire) caused by excessive wear, indicating the end of service life (such that the PPE should be retired or repaired). Conventionally, within industry, PPE may lack such ESLD which could lead to early retirement of the PPE (increasing costs), late retirement of the PPE (increasing safety risk), and/or a reduced amount of reuse and product repair. Furthermore, any conventional end of service life testing for PPE may be destructive in nature. In other words, the PPE may have to be pulled apart (e.g. torn/ripped apart, unstitched, etc.) to determine the cause of failure. Generally, this may lead to disposal of the PPE rather than reuse of it (due to the costs/time associated with repairing the product after taking/pulling it apart). Additionally, conventional ESLD may require a huge infrastructure with product downtime (e.g. the PPE may not be used for (significant) amounts of time while testing is being conducted). In some cases, the conventional testing methods may not determine the underlying cause of failure and/or the zone of failure. Instead, many conventional tests only allow the user to determine if the PPE is adequate for use and/or if it needs to be disposed/retired (e.g. pass or fail type testing). The Applicants have devised a way to more quickly (e.g. reduced product downtimes) and adequately (e.g. without pulling the PPE apart and/or more precise targeting) determine damage/wear of the PPE (for example, assigning zones to the PPE to determine which specific/unique zone of the PPE needs to be repaired and/or alerting the user if/when the PPE needs to be retired). In the disclosed embodiments, the Applicants have implemented/incorporated magnetic particles into or onto the PPE device (e.g. so as to be distributed within/across at least a portion of the PPE and/or a protective barrier layer/matrix) to allow a magnetic ESLD scan of the device. In some embodiments, the magnetic scan may reveal the magnetic field signature (MFS) of the PPE based on various zones of the PPE (e.g. each zone of the PPE having its own MFS). In this manner, the user may more easily/quickly determine the specific/unique area/zone of the PPE needing repair (without damaging./pulling apart the PPE or having to undergo extensive testing with product downtimes). Additionally, the Applicants have constructed a system and/or method using a test rig with which to conduct a PPE magnetic scan. In some embodiments, the system may comprise a test rig with one or more magnetic sensors (placed in a configuration (e.g. equidistant placement of the magnetic sensors)which allows zonal testing (e.g. each magnetic sensor corresponding to an individual zone) of the PPE). Thus, disclosed embodiments may address one or more of such issues with the conventional ways of determining end of service life of the PPE by decreasing test times, increasing product repair and reuse rates, and identifying/pinpointing which zone of the PPE has incurred damage/wear (to allow repair of that specific zone).

Disclosed embodiments relate to personal protective equipment (PPE) comprising magnetic particles. Typically, the magnetic particles may be of an electrically non-conductive nature (e.g. permanent magnets such as ferrite/ceramic particles), although in some embodiments, the magnetic particles may not be of a non-conductive nature (e.g. for certain PPE uses, and in this case, the particles may be electrically conductive permanent magnets such as Neodynium Iron Boron, Samarium Cobalt, Alnico, etc.). Generally, the type of magnetic particle being implemented into/onto the protective barrier layer/matrix of the PPE may depend on the temperature range within which the PPE is configured/operable to be used (e.g. PPE used within a high temperature range (e.g. 250° C.-550° C.) may comprise Samarium Cobalt magnetic particles). Typically, the size of the magnetic particles may vary from 3-1000 micrometers. However, in some embodiments, the size of the magnetic particles may be larger or (significantly) smaller (e.g. nanoparticles of magnetic materials (e.g. ferrite) enabling the PPE to be (significantly) nonmagnetic and increasing the chances of proper blending (e.g. more homogeneous) of the nanoparticles). Generally, the magnetic particles may be incorporated within the PPE by being blended into a polymeric compound (which might include rubber) (used to form at least a portion of the PPE) (e.g. the protective barrier layer/matrix of the PPE is formed of this blend). Typically, the magnetic particles may comprise approximately 0.01-10 percent of the material (or no more than 10, 20, or 30%) (generally, as low as 0.5% to 40%) within the PPE device (e.g., so that the overall integrity of the PPE is not changed significantly). There are many exemplary ways/methods of incorporating the magnetic particles into the protective barrier layer/matrix of the PPE, some of which will be described below. However, persons of skills will appreciate alternative/additional methods of (substantially homogeneously) incorporating the magnetic particles within the matrix of the PPE (e.g. by adding a patch to the protective barrier layer/matrix of the PPE, stitching thread/filament onto/into PPE, molding PPE from a polymeric compound comprising magnetic particles, coating PPE with a polymeric compound comprising magnetic particles, etc.).

By way of example, personal protective equipment (PPE) may comprise one of the following: a glove, a boot/shoe, a protective suit/clothing, a hood, a fall protection harness, a fall protection lanyard, a knee/elbow pad, etc. Due to the large variety of PPE, there may be several ways/methods of incorporating magnetic particles into the protective barrier layer/matrix of the PPE. Generally, the magnetic particles may be incorporated within the PPE by attaching to the exterior surface of the PPE (e.g. exterior of the protective envelope/surface). Some exemplary ways/methods may comprise (as discussed above): coating the PPE, molding the PPE (e.g. with polymeric compound comprising magnetic particles), and/or extruding a sheet, thread, filament, patch, etc. to be attached onto the protective barrier layer/matrix of the PPE. In some embodiments, coating the PPE may comprise incorporating (substantially homogeneously) the magnetic particles within a polymeric compound. The coating may then be painted/brushed or otherwise applied (e.g. sprayed, rolled on, dipped, etc.) onto the PPE at least in areas of high wear (e.g. seams, knees, elbows, etc.). In some embodiments, the coating may be applied to a separate fabric and then attached to the PPE (e.g. coating a patch of fabric or other material (e.g. patch) and attaching the fabric or other material to the PPE (e.g. by adhesive, stitching, embroidery, etc)). In some embodiments, molding the PPE may comprise mixing the magnetic particles within the polymer (which could include rubber) matrix and using a mold of the PPE to dip into the liquid mixture (e.g. bath) of the polymeric (or rubber) compound to form the PPE needed (after allowing it to cool/solidify). Additionally, molding the PPE may occur by pouring the liquid mixture of the polymeric compound comprising magnetic particles into a mold of the PPE (and allowing the mixture to cool/solidify) to form the PPE. In some embodiments, the polymeric compound comprising the magnetic particles may be extruded into sheets, filaments, or other components which may be laminated, inter-woven, stitched, and/or attached onto the PPE. Typically, the extrusion matrix formed of a polymeric compound may comprise commodity polymers like rubber, Polyamide, Polyester, Polypropylene, or high end functional polymers such as Aramid, Ultra-High-Molecular-Weight Polyethylene (UHMWPE), etc. In some embodiments, the extruded compound may be used to form filament/fiber (e.g. thread) which can be woven/stitched into the PPE matrix. Additionally, the thread may be used to form an embroidery patch (woven/stitched from the thread) and then attached onto the PPE (e.g. high wear areas of the PPE (e.g. knee or elbow areas)). Generally, the particle density may be 4-15 magnetic particles per inch or, more broadly, 1-30 magnetic particles per inch. Typically, the filament/thread may range from 50 to 1000 deniers which may be multiplied to reach higher deniers (depending on the specific application of the filament/thread in the PPE). In some embodiments, once the magnetic particles are incorporated into the PPE using one of the exemplary methods discussed above (or another exemplary method a person of skill deems possible), a wireless communication element and/or an identifier element may be attached to (the exterior of) the PPE. The incorporation of a wireless communication and/or an identifier element will be further discussed below (after discussion of the test rig).

Typically, in the disclosed embodiments, each PPE comprising the magnetic particles may have a unique/individual magnetic field signature (MFS). In some embodiments, however (for example, if PPE production can be significantly precise), a plurality of (e.g. all of) the PPE (of the same type—e.g. identical) may be manufactured to have the same MFS (e.g. the manufacturing technique of the PPE comprising the magnetic particles is advanced enough to allow (consistent) homogeneous distribution of the magnetic particles for each PPE (of the same type) being manufactured). Typically, if the PPE (of the same type—e.g. identical) has the same MFS, individual PPE may not have to undergo an initial magnetic scan (for example, within a test rig) to determine its unique initial MFS. However, in some embodiments (e.g. when each PPE will have its own unique MFS), once the magnetic particles are incorporated within the PPE, the (initial) MFS may be measured/mapped out within a test rig in 3D (e.g. x-y-z axis). Typically, the test rig may comprise one or more magnetic sensors to determine the MFS (and may be equipped with magnetic sensors which normalize the effect of earth's magnetic field on the test rig). In some embodiments, the one or more magnetic sensors may correspond to an individual zone of the PPE. In this manner, when testing the MFS of the PPE, the test rig may be able to determine the MFS of each individual zone of the PPE (later allowing the user to determine which zone of the PPE incurred the most damage/wear (e.g. the difference between the initial MFS and the current MFS being greater than a pre-determined/pre-set threshold)). Typically, there may exist a correlation between the change in the MFS and the amount of wear on the (same type of) PPE (e.g. when comparing the change (e.g. decrease in MFS) after wearing/using the PPE within the field). In some embodiments, the MFS (e.g. Gauss level) may change linearly with regards to the thickness of the PPE. Generally, for each type of PPE (e.g. gloves, shoes, pants, etc.) there may be a correlation between the change in MFS and the thickness of the PPE. By also tracking the amount of time the PPE is being worn/used, another correlation between time, change in MFS, and thickness of PPE may be calculated/determined. In this manner, the user may be informed/alerted/warned when the PPE may require disposal or repair (while the indication of wear is still within a safety factor).

In some embodiments, the test rig may comprise a mannequin element (e.g. corresponding to the type of PPE being tested) (or other support element operable/configured to hold the PPE in a fixed position for sensing the MFS) so that the corresponding PPE may be placed on the mannequin element during testing. This may allow the PPE to have a fixed location/orientation/position with respect to the sensors (so that while conducting individual tests (e.g. at different times) to determine the MFS of the PPE, the zones for testing are not changed with respect to the initial location/orientation/position of the (PPE). Additionally, in some embodiments, the shape of the mannequin element may vary depending on the shape of the respective PPE. In some embodiments, the mannequin element may be a stand (e.g. not necessarily taking the shape of the PPE). Generally, once the (initial) MFS is determined by the test rig, the test rig may communicate the sensor data (e.g. Gauss levels) to a processor to store the sensor data. In some embodiments, the processor may be located within the test rig. In some embodiments, the sensor data (for each zone) may be stored onto the PPE comprising an identification element and/or a wireless communication element. In other embodiments, the sensor data (for each zone) may be stored onto a processor located within a handheld/portable device or a computer. Typically, transmission of sensor data from the test rig to the PPE, handheld/portable device, or computer may take place via a (wireless) transmitter.

In the disclosed embodiments, the magnetic field signature (MFS) data (e.g. Gauss levels) may be stored onto the PPE comprising an identifier element and/or a wireless communication element. In some embodiments, the identifier element and/or the wireless communication element may be located on the exterior of the PPE (for quick identification and/or allowing linking/quick reference to stored MFS for that PPE). In some embodiments, the identifier element may be a barcode or a serial number. The identifier element may be important in identifying the particular PPE when the MFS of the (same type of) PPE may vary (e.g. if the manufacturing technique doesn't allow for homogeneous distribution of the magnetic particles for all PPE of the same type). In some embodiments, some manufacturing techniques may be able to allow homogeneous distribution of magnetic particles. Thus, the identifier element may not be required. In some embodiments, the wireless communication element (e.g. near field communication (NFC) patch) may comprise a memory storage storing the (initial) MFS data transmitted from the test rig (and the identifier information, in which case the identifier element may be optional). With the wireless communication element attached to the PPE, a user may be able to determine the individual PPE's MFS data without searching through a database. This may increase testing speeds and allow for accurate determination of changes (e.g. decrease) in MFS due to wear/damage (e.g. less room for human error).

In the disclosed embodiments, the test rig (which may be portable) may be configured to interact with a handheld/portable device (and/or a processor/computer), for example when used in the field to check the service life of the PPE. In some embodiments, the handheld/portable device (and/or a processor/computer) may warn the user if/when the PPE is estimated (based on a scan by the test rig) to have too much damage to be considered usable within the field (e.g. when the PPE should be disposed and/or repaired). This may be accomplished as a result of the decrease in MFS for the (same type of) PPE having a correlation (e.g. linear the amount of wear/damage being incurred by the PPE (as discussed in more detail previously). Thus, in some embodiments, the user may be forewarned to dispose or fix/repair the PPE. Typically, the user may be alerted of end of service life of the PPE while still maintaining the safety factor for the PPE (in other words, the user would be alerted to dispose/repair the PPE a little before (e.g. within a certain threshold/safety factor) the PPE is actually considered to be expendable). While persons of skill should understand the disclosed embodiments based on the above disclosure, the following figures may provide specific examples that may further clarify the disclosure.

Turning now to the drawings, FIG. 1 illustrates a planar view of an exemplary embodiment of a personal protective equipment (PPE) matrix 101 comprising magnetic particles 102 distributed (substantially) homogeneously across the PPE. As discussed above, the magnetic particles 102 may typically be non-conductive in nature (e.g. ferrite/ceramic magnetic particles). In some embodiments, however, the magnetic particles 102 may be conductive in nature (e.g. Neodynium Iron Boron, Samarium Cobalt, Alnico, etc.). Generally, the type of magnetic particle 102 being implemented into/onto the PPE may depend on the temperature range within which the PPE is configured/operable to be used. Typically, the size of the magnetic particles 102 may vary from 3-1000 micrometers. However, in some embodiments, the size of the magnetic particles 102 may be larger or (significantly) smaller (e.g. nanoparticles of magnetic materials (e.g. ferrite) enabling the PPE to be (significantly) nonmagnetic and increasing the chances of proper blending (e.g., more homogeneous) of the nanoparticles). Typically, the magnetic particles 102 may comprise approximately 0.01-10 percent of the material (or no more than 10, 20, or 30%) (generally, as low as 0.5% to 40%) within the PPE device (e.g. so that the overall integrity of the PPE is not changed significantly). In some embodiments, when the magnetic particles 102 comprise more than 40% of the PPE material and/or the structural integrity of the PPE may be transformed, proper testing of the product may take place to ensure the PPE performs to adequately protect the user. In the embodiment of FIG. 1, the magnetic particles 102 are shown to be (substantially) homogeneously distributed within a matrix 101. Generally, the matrix 101 may be formed of a polymeric (for example, rubber) compound. In the embodiment of FIG. 1, the magnetic particles 102 are blended within the polymeric compound via a batch process (e.g. to prevent particle agglomeration and to ensure substantially homogeneous mixing). Typically, the mixture of the polymeric compound with the magnetic particles 102 (e.g. matrix 101) may be a liquid. Generally, after some time, the liquid may solidify as it cools down. In the embodiment shown in FIG. 1, the matrix 101 comprising the magnetic particles 102 is formed into a sheet. In some embodiments, the mixture may be used to directly coat the PPE (e.g. while the polymeric compound comprising the magnetic particles 102 is still in the liquid phase). For example, the coating may be painted/brushed onto the PPE in areas of high wear (e.g. seams, knees, elbows, etc.). In some embodiments, the coating may be applied to a separate fabric and then attached to the PPE (e.g. patch). In some embodiments, the mixture (of polymeric compound and magnetic particles 102) may be used to mold the PPE. Typically, a mold of the PPE may be used to dip into the liquid mixture (e.g. bath) of the polymeric compound to form the PPE needed (after allowing it to cool/solidify).

Figure 2A:
FIG. 2A illustrates a cross-sectional view of an exemplary embodiment of a polymeric or rubber compound comprising magnetic particles extruded into a thread/filament.

FIG. 2A illustrates a planar view of an exemplary embodiment of a polymeric (or rubber) compound comprising magnetic particles 202 extruded into a thread/filament 205. In the embodiment of FIG. 2A, the magnetic particles 202 are similar to those discussed in reference to FIG. 1. However, in the embodiment of FIG. 2A, the polymeric compound comprising the magnetic particles 202 are shown to be extruded into thread/filament 205. In some embodiments, the polymeric compound may be extruded into thread/filament 205 (as shown in FIG. 2A), sheets, or other components which may be laminated, inter-woven, stitched, and/or attached onto the PPE. Typically, the extrusion material may be formed of a polymeric compound comprising commodity polymers like rubber, Polyatnide, Polyester, Polypropylene, or high end functional polymers such as n-Aramid, UHMWPE, etc. As shown in the embodiment of FIG. 2A, the extruded compound may be used to form filament/fiber/thread 205. The filament/thread 205 shown in the embodiment of FIG. 2A may comprise 50 to 1000 deniers (which may be multiplied/combined to reach higher deniers depending on the application of the filament fiber 205). Generally, increasing the number of deniers results in an increase in thickness of the filament/fiber 205.

Figure 2B:
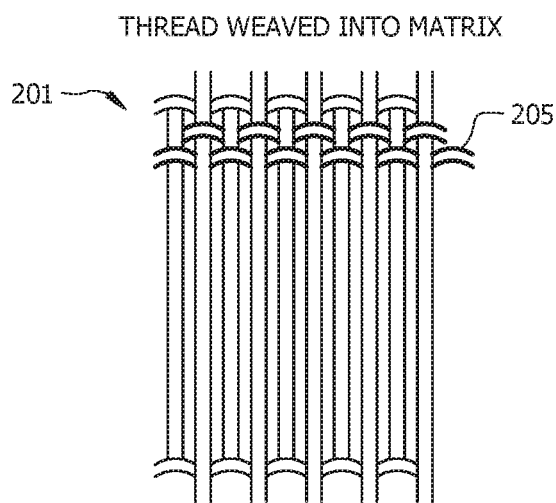
FIG. 2B illustrates a perspective view of an exemplary embodiment of a thread/filament (similar to the exemplary embodiment shown in FIG. 2A) woven/stitched into a PPE matrix (e.g. of PPE matrix material thread)

FIG. 2B illustrates a planar view of an exemplary embodiment of a thread/filament 205 (similar to the exemplary embodiment shown in FIG. 2A) being weaved/stitched into a matrix 201 of the PPE. Generally, the particle density may be 4-15 magnetic particles per inch or, more broadly, 1-30 magnetic particles per inch. Alternatively, the thread/filament 205 might be used at the seams of the PPE (since the seams tend to be high wear areas). So, for example, the thread/filament 205 might be used to sew the seams of the PPE.

Figure 3:
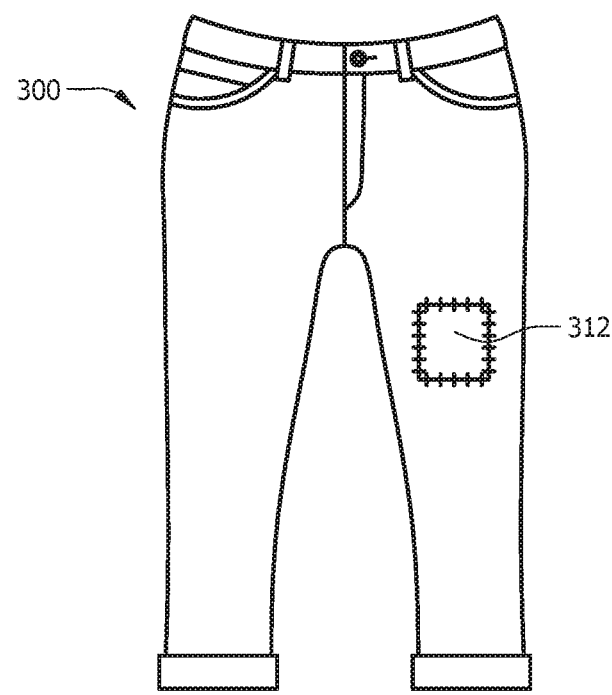
FIG. 3 illustrates a front view of an exemplary embodiment of a PPE comprising a patch formed from the polymeric (or rubber) compound comprising the magnetic particles.

FIG. 3 illustrates a planar view of an exemplary embodiment of a PPE 300 comprising a patch 312 formed from the polymeric (or rubber) compound comprising the magnetic particles. The thread/filament (shown in FIG. 2A) may be used to form the embroidery patch 312 which may then be attached (e.g. stitched or glued) onto the (high wear areas (e.g. knees, elbows, seams, etc.)) of the PPE 300.

Figure 4:
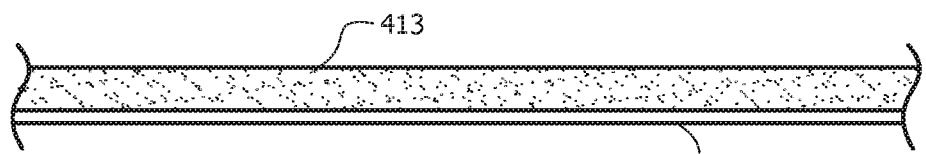
FIG. 4 illustrates a cross-sectional view of an exemplary embodiment of a PPE coated with a polymeric compound comprising magnetic particles.

FIG. 4 illustrates a cross-sectional view of an exemplary embodiment of a PPE material 411 coated with a polymeric compound comprising magnetic particles 413. Typically, a PPE material 411 may be coated with the polymeric compound comprising the magnetic particles 413 as discussed in reference to FIG. 1. The coating may be applied directly onto the PPE material 411 (e.g. on high wear areas (e.g. elbows, knees, seams, etc.)) or the coating ay be applied to an individual sheet of material (e.g. fabric, plastic, etc.) and the individual sheet may be attached (e.g. stitched onto) to the PPE material 411 and/or formed into the PPE material 411.

Figure 5A:
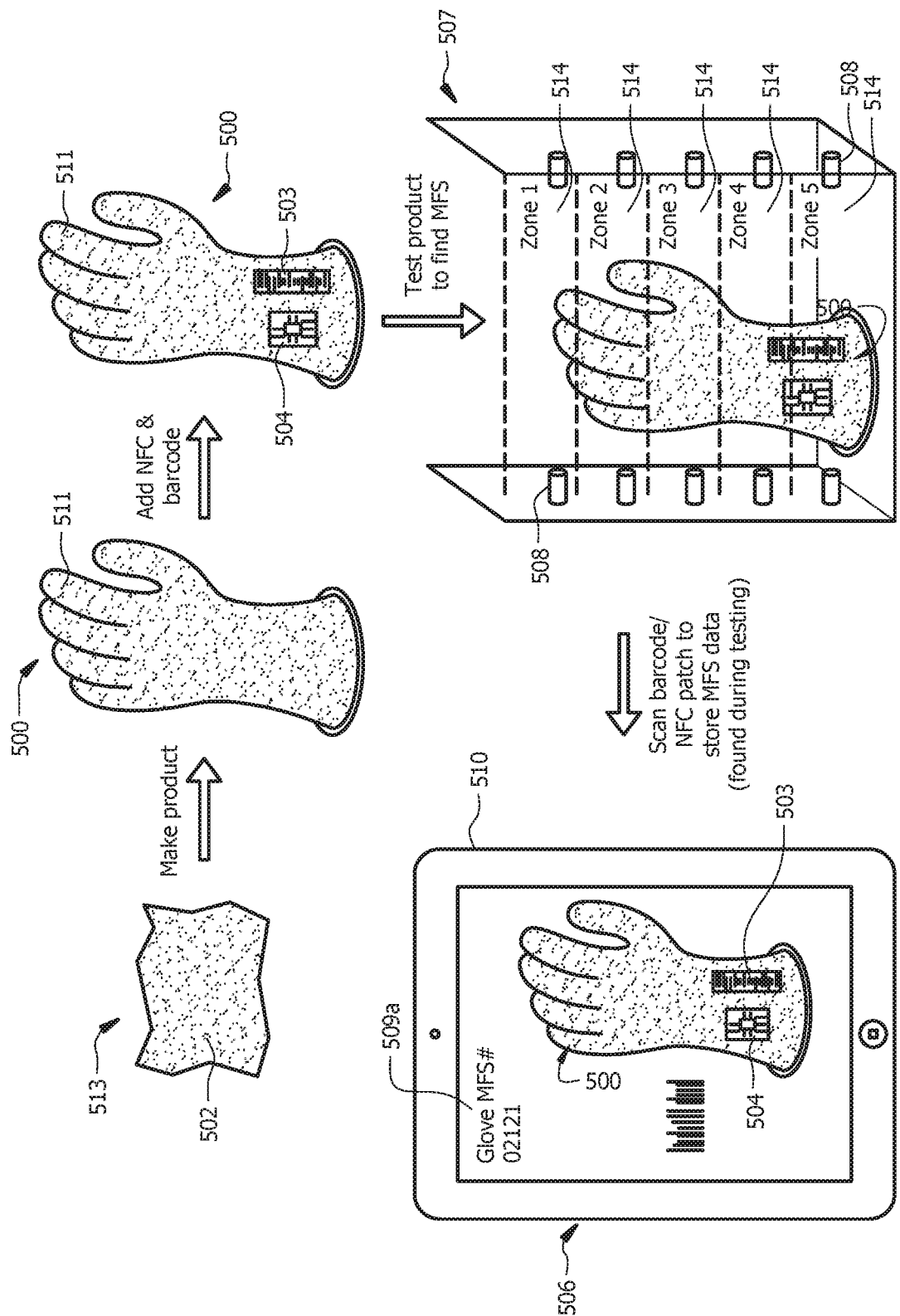
FIG. 5A illustrates a schematic of an exemplary method of forming a PPE device comprising magnetic particles, an identifier element, a wireless communication element, and an initial magnetic field signature (MFS) using a test rig and a handheld/portable device.

FIG. 5A illustrates a schematic of an exemplary method of forming a PPE device 500 comprising magnetic particles 502, two identifier elements (e.g. NFC patch, barcode, etc.) 503, 504, and an initial MFS 509a using a test rig 507 and a handheld/portable device 510. Typically, the magnetic particles 502 may be incorporated into a polymeric compound 513 to form a matrix. As discussed in reference to FIG. 1-FIG. 4, there may be several ways/methods of incorporating the magnetic particles 502 within the PPE 500. Some of the methods/ways may include (but are not limited to) the following: forming (e.g. extruding) the polymeric compound 513 (with magnetic particles 502) into thread/filament and sewing the thread into the PPE 500 or adding the thread to the weave of the material used to form the PPE 500 or sewing (into embroidery pattern) the thread onto a patch and affixing the patch onto the PPE 500; forming a coating material of the polymeric compound 513 with magnetic particles 502 and coating (at least a portion of) the PPE 500 with the coating material; dipping (one or more times) a mold of the PPE 500 into a liquid (e.g. bath) of the polymeric compound 513 with magnetic particles 502 (and allowing it to cool/solidify) to form the PPE 500; adding molten polymeric compound 513 with magnetic particles 502 into a mold for the PPE 500; mixing magnetic particles 502 into the polymeric compound 513 from which the PPE 500 is to be formed; extruding a sheet of material (from which to form the PPE 500, e.g. by cutting and sewing) from molten polymeric compound 513 with magnetic particles 502 distributed (e.g. substantially homogeneously) throughout; and combinations thereof. In the exemplary method of FIG. 5A, a wireless communication element 504 and/or an identifier element 503 may be attached to the PPE 500 (e.g. for uniquely identifying the specific PPE 500 to which it corresponds and/or the MFS 509a). In the embodiment of FIG. 5A, the wireless element 504 is a near field communication (NFC) patch configured to receive the output signal (indicative of initial MFS 509a) from the test rig 507 and/or store the initial MFS 509a of the PPE 500 on the wireless communication element 504 (having memory storage). In the embodiment of FIG. 5A, the identifier element 503 may be a barcode (in other embodiments, the identifier element 503 may be a serial number). Generally, the identifier element 503 may be linked to a memory storage (e.g. on a processor 506 located within a computer, handheld/portable device 510, and/or the test rig 507). Some PPE 500 embodiments may have only one of the wireless elements 504 or the identifier element 503. To find the initial MFS 509a, the PPE 500 is typically placed in a test rig 507, for example having a mannequin element (so that any testing sensor scanning will be repeatable since the PPE 500 will be supported/held in a specific repeatable configuration (e.g. with respect to the sensors 508 of the test rig 507)). In the embodiment of FIG. 5A, the test rig 507 is shown to have 5 zones 514 each with its own sensor 508. In the embodiment of FIG. 5A, the MFS 509a of the PPE 500 is determined via zones 514 and communicated to a handheld/portable device 510 via wireless communication 504 (e.g. Wi-Fi, Bluetooth, etc) (although in other embodiments, the MFS 509a might be transmitted to some other processor 506 (for example, within the test rig 507)).

Figure 5B:
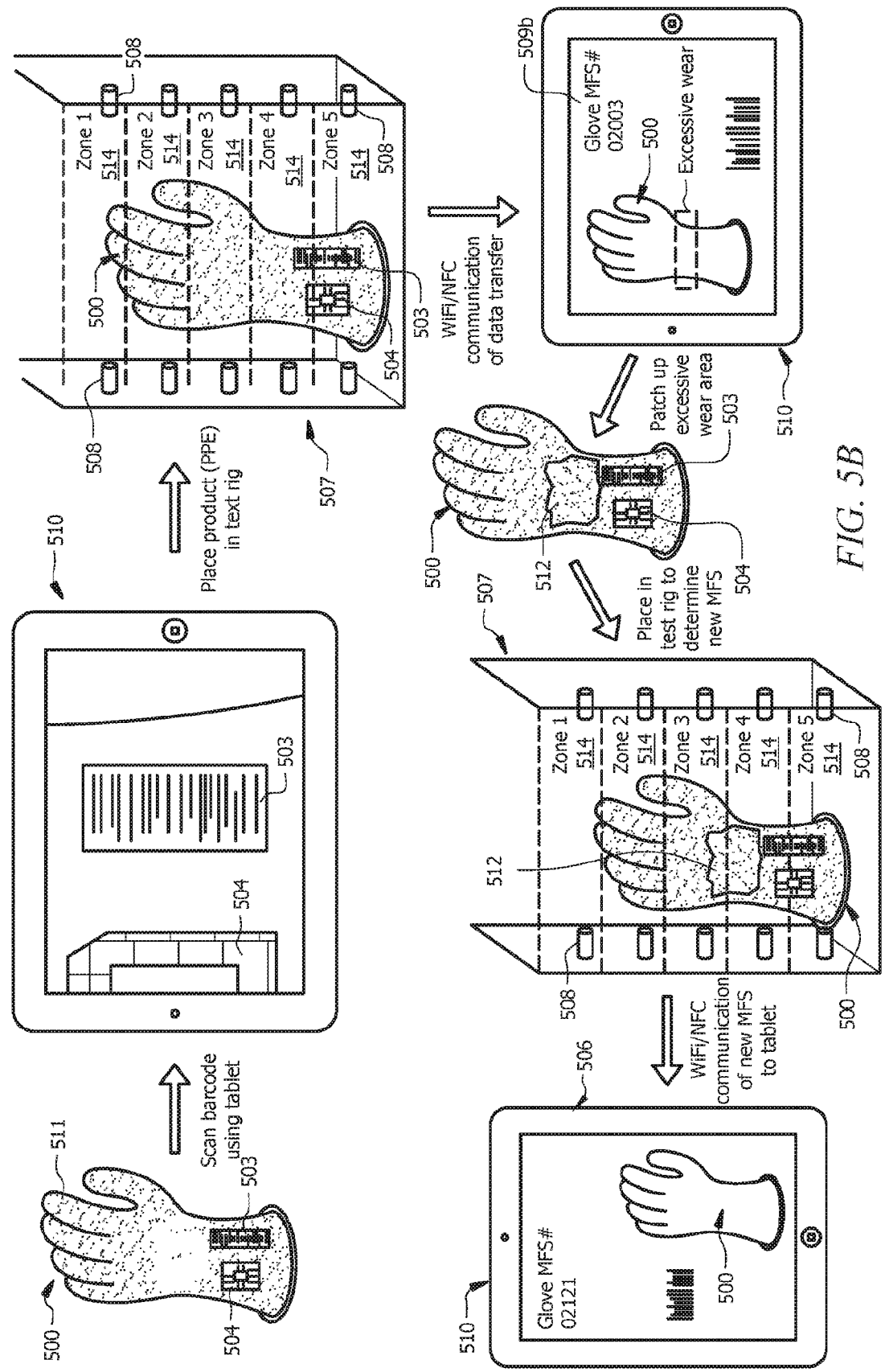
FIG. 5B illustrates a schematic of an exemplary method of determining end of service life for a PPE comprising magnetic particles, an identifier element, a wireless communication element, and an initial MFS using a test rig and a handheld/portable device.

FIG. 5B illustrates a schematic of an exemplary method of determining end of service life for a PPE 500 comprising magnetic particles, two identifier elements (e.g. NFC patch, barcode, etc.) 503, 504, and an initial magnetic field signature (MFS) 509a using a test rig 507 and a handheld/portable device 510. In the embodiment of FIG. 5B, the PPE device 500 may be previously worn. Thus, further testing may be conducted to determine if the PPE 500 has reached end of service life. Thus, the initial MFS 509a for (e.g. associated with) the PPE 500 may be retrieved by a processor 506 (for example, comprised within the handheld/portable device 510 (e.g, by scanning the barcode and/or wirelessly communicating with the PPE 500 via the NFC patch)). In the embodiment of FIG. 5B, the PPE 500 is then placed in the test rig 507 which could be the same test rig 507 as used for the initial MFS 509a determination (similar to the method discussed in FIG, 5A) or could be an identical test rig 507 (e.g. configured identically to the test rig 507 for the initial MFS 509a determination)) and the sensor 508 data is sent as output signals to the processor 506, for example, in the handheld/portable device 510. As shown in FIG. 5B, the processor 506 (e.g. handheld/portable device 510) may include an end of service life profile for the PPE 500. Typically, the profile may indicate that the PPE 500 has reached its end of service life (e.g. should be retired, replaced, or repaired)—such profile may typically be predetermined by (e.g. pre-set using) testing to correlate a decrease in MFS 509a, 509b to end of service life (preferably in a way that indicates end of service life while still maintaining the safety factor for the PPE 500). In the embodiment of FIG. 5B, the test rig 507 is configured to indicate/alert the user when a certain zone 514 of the PPE 500 has excessive wear (e.g. reached end of service life) and needs to be replaced and/or fixed. Generally, evaluating/determining, service life of PPE 500 comprises using the comparison of the current MFS 509b of the PPE 500 to the initial MFS 509a of the PPE 500 and the end of service life profile (which might indicate the amount (either raw or percentage) of change from the initial MFS 509a that would be indicative of end of service life) to evaluate life of the PPE 500 (e.g. determine whether the end of service life has been reached). In the embodiment of FIG. 5B, the PPE 500 is shown to have excessive wear (e.g. on the protective barrier layer 511 of the PPE 500) and undergoes fixing/repairing of the zone 514 of wear (e.g. in such a way as to restore the PPE 500 service life so that it operable to be put back into use in the field). Once the PPE 500 is repaired (in the embodiment of FIG. 5B, the repair is conducted by adding a patch 512 to the PPE 500), the repaired PPE 500 undergoes testing to determine that the repair has been successful (and, in some embodiments, to determine the new MFS of the PPE 500 (e.g. for at least the repaired zone of the PPE 500)).

Figure 6:
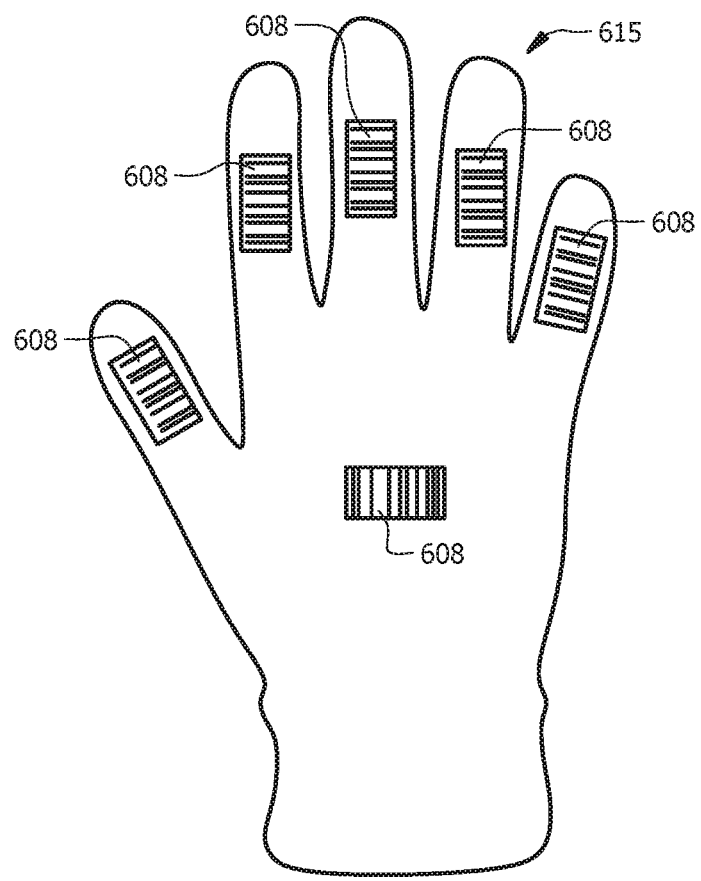
FIG. 6 illustrates a front view of an exemplary embodiment of a mannequin element comprising six sensors for use within a test rig.

FIG. 6 illustrates a planar view of an exemplary embodiment of a mannequin element 615 comprising six sensors 608 for use within a test rig. Unlike the mannequin element 608 shown in the exemplary embodiment of a test rig in FIG. 5A-FIG. 5B, the mannequin element 615 of FIG. 6 comprises the sensors 608 located on the mannequin element 615 rather than on the enclosing structure of the test rig. For some types of PPE (e.g. gloves), it may be more convenient to locate the sensors 608 on the mannequin element 615 to allow for more accurate placement of the PPE while attempting to repeat the tests (e.g. over time). However, for other types of PPE (e.g. shoes), it may be more convenient to place the sensors on the test rig.

Having described device, method, and system embodiments above, especially with regard to the figures, various additional embodiments can include, but are not limited to the following:

In a first embodiment, a personal protective equipment (PPE) device comprising: (a protective barrier layer of material—e.g. configured to form a protective envelope/surface); magnetic particles; an identifier element; and/or (a wireless communication element); wherein: the magnetic particles are incorporated within or attached/affixed to (at least a portion of) (e.g. so as to be distributed within/across the PPE and/or the protective barrier layer—e.g. in a manner forming a (distinctive) magnetic field signature (MFS)) the PPE; the identifier element is attached to the (exterior of the) PPE; and/or (the wireless communication element is attached to the (exterior of the) PPE). A second embodiment can include the PPE device of the first embodiment, wherein the wireless communication element comprises memory/storage to store initial MFS information of the PPE (and a wireless transmitter). A third embodiment can include the PPE device of the first to second embodiments, wherein the identifier element is configured to uniquely identify the PPE (allowing linkage to initial MFS information of the PPE, for example via Wi-Fi upon scanning of the identifier element). A fourth embodiment can include the PPE device of the first to third embodiments, wherein the magnetic particles comprise electrically non-conductive magnetic particles. A fifth embodiment can include the PPE device of the first to fourth embodiments, wherein the magnetic particles range from 3-1000 micrometers. A sixth embodiment can include the PPE device of the first to fifth embodiments, wherein the magnetic particles are incorporated within the PPE by being blended into a polymeric compound or rubber (used to form at least a portion of the PPE) (e.g. the protective barrier layer of the PPE is formed of this blend). A seventh embodiment can include the PPE device of the first to sixth embodiments, wherein the magnetic particles are distributed in an (underlying) matrix of a material of the PPE (e.g. the polymeric material or the rubber material forming the protective barrier layer of the PPE). An eighth embodiment can include the PPE device of the first to seventh embodiments, wherein the PPE is configured to be molded from the polymeric compound or rubber comprising the magnetic particles. A ninth embodiment can include the PPE device of the first to eighth embodiments, wherein the PPE is formed by dipping (one or more times) a mold of the PPE into a liquid (e.g. bath) of the polymeric compound (or rubber) with magnetic particles (and allowing it to cool/solidify) to form the PPE (with magnetic particles distributed). A tenth embodiment can include the PPE device of the first to ninth embodiments, wherein the polymeric compound (or rubber comprising the magnetic particles is configured to be extruded into thread/filament, and wherein the thread/filament is stitched into a matrix of a material of the PPE device. An eleventh embodiment can include the PPE device of the first to tenth embodiments, wherein the thread/filament is woven into fabric material forming the protective barrier layer of the PPE in a grid (e.g. thread forms a grid-like structure—the grid size may vary from 0.5 cm×0.5 cm to 5 cm×5 cm). A twelfth embodiment can include the PPE device of the first to eleventh embodiments, wherein the thread/filament is used for one or more seams on the PPE (since seams are a high wear area). A thirteenth embodiment can include the PPE device of the first to twelfth embodiments, wherein the polymeric compound or rubber comprising the magnetic particles is configured to be coated onto (e.g. applied to a surface of) the PPE device. A fourteenth embodiment can include the PPE device of the first to thirteenth embodiments, wherein such coating is located on the exterior surface of the PPE (e.g. exterior of the protective envelope/surface). A fifteenth embodiment can include the PPE device of the first to fourteenth embodiments, wherein the magnetic particles are incorporated/located within patches (e.g. affixed to the exterior of the PPE). A sixteenth embodiment can include the PPE device of the first to fifteenth embodiments, wherein the patches comprise embroidery with thread/filament comprising magnetic particles. A seventeenth embodiment can include the PPE device of the first to sixteenth embodiments, wherein the thread/filament forms a specific design/shape. An eighteenth embodiment can include the PPE device of the first to seventeenth embodiments, wherein the PPE is one of the following: glove, boot/shoe, protective suit/clothing, hood, fall protection harness, fall protection lanyard, knee/elbow pad, etc. A nineteenth embodiment can include the PPE device of the first to eighteenth embodiments, wherein the magnetic particles are only incorporated into a portion of (protective envelope or surface of) the PPE (e.g. at high wear locations, such as knees or elbows). A twentieth embodiment can include the PPE device of the first to nineteenth embodiments, wherein the (initial) MFS is measure in 3D (e.g. x-y-z axis). A twenty-first embodiment can include the PPE device of the first to twentieth embodiments, wherein the magnetic particles comprise approximately 0.01-10 percent of the material (or no more than 10, 20, or 30%) within the PPE device (e.g. so that the overall integrity of the PPE is not changed significantly). A twenty-second embodiment can include the PPE device of the first to twenty-first embodiments, wherein the identifier element comprises a near-field communication (NFC) tag. A twenty-third embodiment can include the PPE device of the first to twenty-second embodiments, wherein the identifier element comprises a barcode. A twenty-fourth embodiment can include the PPE device of the first to twenty-third embodiments, wherein the identifier element comprises a serial number. A twenty-fifth embodiment can include the PPE device of the first to twenty-fourth embodiments, wherein the PPE comprising the magnetic particles further comprises its own (e.g. unique) (initial) MFS. A twenty-sixth embodiment can include the PPE device of the first to twenty-fifth embodiments, wherein the MFS comprises a plurality of zones, each having its own magnetic reading. A twenty-seventh embodiment can include the PPE device of the first to twenty-sixth embodiments, wherein the magnetic particles are distributed (substantially homogeneously or evenly) across the PPE and/or for each MFS zone of the PPE.

Exemplary embodiments might also relate to a system for determining end of service life (ESLD) of a personal protective equipment (PPE) (e.g. similar to those described above, which may be considered optionally incorporated herein with respect to the discussion of the system). Such system embodiments, for example, might include, but are not limited to, the following:

In a twenty-eighth embodiment, an end of service life determination (ESLD) system comprising: a personal protective equipment (PPE); a processor; and a test rig; wherein: the test rig further comprises one or more magnetic sensors (and a (wireless) transmitter configured to send magnetic field signature (MFS) data to the processor); the PPE further comprises: magnetic particles; an identifier element; and/or a wireless communication element; wherein: the magnetic particles are incorporated within or attached/affixed to (at least a portion of) (e.g. so as to be distributed within/across the PPE and/or the protective barrier layer—e.g. in a manner forming a (distinctive) MFS) the PPE; the identifier element is attached to the (exterior of the) PPE; and/or (the wireless communication element is attached to the (exterior of the) PPE; the processor is configured to receive (and store) MFS sensor data from the test rig and compare the received sensor data with initial (pre-existing) MFS associated with the PPE. A twenty-ninth embodiment can include the system of the twenty-eighth embodiment, wherein the wireless communication element comprises memory/storage to store initial MFS information of the PPE (and a wireless transmitter). A thirtieth embodiment can include the system of the twenty-eighth to twenty-ninth embodiments, wherein the identifier element is configured to uniquely identify the PPE (allowing linkage to initial MFS information of the PPE, for example via Wi-Fi upon scanning of the identifier element). A thirty-first embodiment can include the system of the twenty-eighth to thirtieth embodiments, wherein the magnetic particles comprise electrically non-conductive magnetic particles. A thirty-second embodiment can include the system of the twenty-eighth to thirty-first embodiments, wherein the magnetic particles range from 3-1000 micrometers. A thirty-third embodiment can include the system of the twenty-eighth to thirty-second embodiments, wherein the magnetic particles are incorporated within the PPE by being blended into a polymeric compound or rubber (used to form at least a portion of the PPE) (e.g. the protective barrier layer of the PPE is formed of this blend). A thirty-fourth embodiment can include the system of the twenty-eighth to thirty-third embodiments, wherein the magnetic particles are distributed in an (underlying) matrix of a material of the PPE (e.g. the polymeric material or the rubber material forming the protective barrier layer of the PPE). A thirty-fifth embodiment can include the system of the twenty-eighth to thirty-fourth embodiments, wherein the PPE is configured to be molded from the polymeric compound or rubber comprising the magnetic particles. A thirty-sixth embodiment can include the system of the twenty-eighth to thirty-fifth embodiments, wherein the PPE is formed by dipping (one or more times) a mold of the PPE into a liquid (e.g. bath) of the polymeric compound (or rubber) with magnetic particles (and allowing it to cool/solidify) to form the PPE (with magnetic particles distributed). A thirty-seventh embodiment can include the system of the twenty-eighth to thirty-sixth embodiments, wherein the polymeric compound (or rubber) comprising the magnetic particles is configured to be extruded into thread/filament, and wherein the thread/filament is stitched into a matrix of a material of the PPE device. A thirty-eighth embodiment can include the system of the twenty-eighth to thirty-seventh embodiments, wherein the thread/filament is woven into fabric material forming the protective barrier layer of the PPE in a grid (e.g. thread forms a grid-like structure—the grid size may vary from 0.5 cm×0.5 cm to 5 cm×5 cm). A thirty-ninth embodiment can include the system of the twenty-eighth to thirty-eighth embodiments, wherein the thread/filament is used for one or more seams on the PPE (since seams are a high wear area). A fortieth embodiment can include the system of the twenty-eighth to thirty-ninth embodiments, wherein the polymeric compound or rubber comprising the magnetic particles is configured to be coated onto (e.g. applied to a surface of) the PPE device. A forty-first embodiment can include the system of the twenty-eighth to fortieth embodiments, wherein such coating is located on the exterior surface of the PPE (e.g. exterior of the protective envelope/surface). A forty-second embodiment can include the system of the twenty-eighth to forty-first embodiments, wherein the magnetic particles are incorporated/located within patches (e.g. affixed to the exterior of the PPE). A forty-third embodiment can include the system of the twenty-eighth to forty-second embodiments, wherein the patches comprise embroidery with thread/filament comprising magnetic particles. A forty-fourth embodiment can include the system of the twenty-eighth to forty-third embodiments, wherein the thread/filament forms a specific design/shape. A forty-fifth embodiment can include the system of the twenty-eighth to forty-fourth embodiments, wherein the PPE is one of the following: glove, boot/shoe, protective suit/clothing, hood, fall protection harness, fall protection lanyard, knee/elbow pad, etc. A forty-sixth embodiment can include the system of the twenty-eighth to forty-fifth embodiments, wherein the magnetic particles are only incorporated into a portion of (protective envelope or surface of) the PPE (e.g. at high wear locations, such as knees or elbows). A forty-seventh embodiment can include the system of the twenty-eighth to forty-sixth embodiments, wherein the (initial) MFS is measure in 3D (e.g. x-y-z axis). A forty-eighth embodiment include the system of the twenty-eighth to forty-seventh embodiments, wherein the magnetic particles comprise approximately 0.01-10 percent of the material (or no more than 10, 20, or 30%) within the PPE device (e.g. so that the overall integrity of the PPE is not changed significantly). A forty-ninth embodiment can include the system of the twenty-eighth to forty-eighth embodiments, wherein the identifier element comprises a near-field communication (NFC) tag. A fiftieth embodiment can include the system of the twenty-eighth to forty-ninth embodiments, wherein the identifier element comprises a barcode. A fifty-first embodiment can include the system of the twenty-eighth to fiftieth embodiments, wherein the identifier element comprises a serial number. A fifty-second embodiment can include the system of the twenty-eighth to fifty-first embodiments, wherein the PPE comprising the magnetic particles further comprises its own (e.g. unique) (initial) MFS. A fifty-third embodiment can include the system of the twenty-eighth to fifty-second embodiments, wherein the magnetic particles are distributed (substantially homogeneously or evenly) across the PPE and/or for each MFS zone of the PPE. A fifty-fourth embodiment can include the system of the twenty-eighth to fifty-third embodiments, wherein the magnetic sensor(s) in the test rig are configured to measure Gauss level (e.g. in a plurality of directions, for example in 3D (x-y-z axis)). A fifty-fifth embodiment can include the system of the twenty-eighth to fifty-fourth embodiments, wherein the processor is comprised within a handheld (portable) wireless device (which might include an output device, such as a display screen, which might be configured to alert the user when the PPE has reached end of service life), and wherein the handheld device comprises a (wireless) receiver configured to receive MFS data from the test rig. A fifty-sixth embodiment can include the system of the twenty-eighth to fifty-fifth embodiments, wherein the handheld/wireless device is configured to communicate with the NFC tag to retrieve (and store) initial MFS data corresponding/associated with the PPE and/or the PPE device identifier information (which might provide linkage to data) (e.g. a scanner or NFC receiver). A fifty-seventh embodiment can include the system of the twenty-eighth to fifty-sixth embodiments, wherein the test rig comprising one or more magnetic sensors is configured to determine the current MFS of the PPE. A fifty-eighth embodiment can include the system of the twenty-eighth to fifty-seventh embodiments, wherein the test rig comprises a plurality of sensors, wherein each test rig zone comprises at least one sensor, and wherein the test rig comprises 4-5 zones. A fifty-ninth embodiment can include the system of the twenty-eighth to fifty-eighth embodiments, wherein the initial MFS of the PPE is determined (and/or pre-set) before use of the PPE (e.g. using the test rig to measure Gauss level for the PPE). A sixtieth embodiment can include the system of the twenty-eighth to fifty-ninth embodiments, wherein the comparison by the processor of the received MFS sensor data to the initial MFS data determines end of service life for the PPE, and an amount of (significant) change (e.g. decrease) in the MFS of the PPE (e.g. current compared to initial) is indicative of wear (and/or damage) of the PPE. A sixty-first embodiment can include the system of the twenty-eighth to sixtieth embodiments, wherein alert/warning is given when comparison (e.g. current compared to initial) indication of wear is still within the safety factor. A sixty-second embodiment can include the system of the twenty-eighth to sixty-first embodiments, wherein there exists a correlation between the change in MFS and the amount of wear of the PPE. A sixty-third embodiment can include the system of the twenty-eighth to sixty-second embodiments, wherein a pre-set amount of change of the MFS (e.g. within one or more zones) is indicative of end of service life for the PPE (resulting in a last notification by the processor). A sixty-fourth embodiment can include the system of the twenty-eighth to sixty-third embodiments, wherein the test rig further comprises a mannequin element (e.g. corresponding to the type of PPE being tested) (or other support element operable/configured to hold the PPE in a fixed position for sensing the MFS), and wherein the PPE is placed on the mannequin element during testing. A sixty-fifth embodiment can include the system of the twenty-eighth to sixty-fourth embodiments, wherein the mannequin element comprises a shape corresponding to the shape of the respective PPE (and a stand, e.g. fixing the location of the PPE with regards to the sensor(s)). A sixty-sixth embodiment can include the system of the twenty-eighth to sixty-fifth embodiments, wherein the test rig is configured so that the mannequin element has a fixed location/orientation/position with respect to the sensors (e.g. allowing respectability). A sixty-seventh embodiment can include the system of the twenty-eighth to sixty-sixth embodiments, wherein the one or more sensors are configured/located/oriented to determine the MFS of the PPE based on the zone in which the one or more sensors are placed (e.g. each zone may have a single sensor associated with their respective zone) (allows mapping of MFS for entire PPE based on zones). A sixty-eighth embodiment can include the system of the twenty-eighth to sixty-seventh embodiments, wherein the test rig is configured to communicate which sensor data is associated/corresponds with each zone of the PPE.

Exemplary embodiments might also relate to a method of forming a personal protective equipment (PPE) comprising magnetic particles and having an initial magnetic field signature (MFS) (e.g. similar to those described above, which may be considered optionally incorporated herein with respect to the discussion of the method). Such method embodiments, for example, might include, but are not limited to, the following:

In a sixty-ninth embodiment, a method of forming a personal protective equipment (PPE) with an initial magnetic field signature (MFS), comprising the steps of: blending (non-conductive) magnetic particles into a polymeric compound; incorporating the polymeric compound with magnetic particles into the (protective barrier layer/envelope of the) PPE (e.g. with the polymeric compound with magnetic particles distributed (e.g. substantially homogeneously) across the PPE or across a portion/zone of the PPE (e.g. for a high-wear area)); placing the PPE (with magnetic particles) into a test rig (comprising a mannequin/support element (configured to support/hold the PPE consistently to allow repeatable sensor scans by fixing the distance between (specific points of) the PPE and the sensors)) and one or more magnetic sensors configured to scan the PPE to determine the initial MFS of the entire PPE or a portion/zone of the PPE (e.g. a high-wear area); determining, via the test rig, the initial MFS of the PPE; (generating (and transmitting), by the test rig, an output signal indicative of the initial MFS of the PPE). A seventieth embodiment can include the method of the sixty-ninth embodiment, wherein incorporating the polymeric compound with magnetic particles into the PPE comprises one of the following: forming (e.g. extruding) the polymeric compound (with magnetic particles) into thread/filament and sewing the thread into the PPE (which might include using the thread to form the seams (e.g. via stitching) of the PPE) or adding the thread to the weave of the material used to form the PPE or sewing (into embroidery pattern) the thread onto a patch and affixing the patch onto the PPE; forming a coating material of the polymeric compound with magnetic particles and coating the PPE (e.g. at least a portion of the PPE and/or one or more patches which are attached to the PPE) with the coating material (with the coating typically applied to the exterior surface of the PPE); dipping (one or more times) a mold of the PPE into a liquid (e.g. bath) of the polymeric compound (e.g. molten) with magnetic particles (and allowing it to cool/solidify) to form the PPE (with magnetic particles distributed); adding molten polymeric compound with magnetic particles into a mold for the PPE (and allowing the material to solidify); mixing magnetic particles into the (matrix of the) (molten/liquid) polymeric compound from which the PPE is to be formed; extruding a sheet of material (from which to form the PPE, e.g. by cutting and sewing) from molten polymeric compound with magnetic particles distributed (e.g. substantially homogeneously) throughout; and combinations thereof. A seventy-first embodiment can include the method of the sixty-ninth to seventieth embodiments, further comprising attaching a wireless communication element and/or an identifier element (e.g. for uniquely identifying the specific PPE to which it corresponds) to the PPE; (receiving the output signal (indicative of initial MFS) from the test rig; and/or storing the initial MFS of the PPE on the wireless communication element (having memory storage, such as a chip (and which might also have a wireless transmitter)) and/or in a memory storage linked/accessible via the identifier element. A seventy-second embodiment can include the method of the sixty-ninth to seventy-first embodiments, wherein placing the PPE into the test rig comprises positioning the PPE on the mannequin element of the test rig (so that any testing/sensor scanning will be repeatable since the PPE will be supported/held in a specific repeatable configuration (e.g. with respect to the sensors of the test rig)). A seventy-third embodiment can include the method of the sixty-ninth to seventy-second embodiments, wherein the MFS of the PPE is determined via zones (e.g. with each zone corresponding to one or more sensor in the test rig and/or a portion of the PPE); and/or wherein the test rig comprises a plurality of sensors (e.g. typically one for each zone). A seventy-fourth embodiment can include the method of the sixty-ninth to seventy-third embodiments, wherein blending the magnetic particles into the polymeric compound comprises distributing (e.g. substantially homogeneously) the magnetic particles throughout the polymeric compound. A seventy-fifth embodiment can include the method of the sixty-ninth to seventy-fourth embodiments, wherein the homogeneous polymeric compound is distributed substantially homogeneously across the PPE and/or a portion/zone of the PPE (such as high wear areas).

Exemplary embodiments might also relate to a method for determining end of service life (ESLD) of a personal protective equipment (PPE) (e.g. similar to those described above, which may be considered optionally incorporated herein with respect to the discussion of the method). Such method embodiments, for example, might include, but are not limited to, the following:

In a seventy-sixth embodiment, a method of determining the end of service life for personal protective equipment (PPE) (having an initial magnetic field signature (MFS), for example with magnetic particles and/or formed using the methods above); comprising the steps of: (wearing, by a user, the PPE); retrieving, by a processor, the initial MFS for (e.g. associated with) the PPE; (retrieving, by the processor, an end of service life profile for the PPE (wherein the profile would be indicative that the PPE has reached its end of service life (e.g. should be retired, replaced, or repaired)—such profile typically being pre-determined by (e.g. pre-set using) testing to correlate a decrease in MFS to end of service life (preferably in a way that indicates end of service life while still maintaining the safety factor for the PPE))); placing the PPE into a test rig (which could be the same test rig as used for the initial MFS determination or could be an identical test rig (e.g. configured identically to the test rig for the initial MFS determination)); determining, by the test rig, the current MFS of the PPE; (generating (and transmitting to the processor), by the test rig a signal indicative of the current MFS of the PPE); evaluating, by the processor, service life of the PPE and/or determining, by the processor, whether the PPE has reached its end of service life (e.g. determining that the PPE has or has not reached an end of service life). A seventy-seventh embodiment can include the method of the seventy-sixth embodiment, wherein evaluating/determining service life of PPE comprises using the comparison of the current MFS of the PPE to the initial MFS of the PPE and the end of service life profile (which might indicate the amount (either raw or percentage) of change from the initial MFS that would be indicative of end of service life) to evaluate life of the PPE (e.g. determine whether the end of service life has been reached). A seventy-eighth embodiment can include the method of the seventy-sixth to seventy-seventh embodiments, wherein the current MFS comprises a plurality of zones (e.g. determined by scanning by one or more sensors associated with each zone/area of the PPE the corresponding zone/area of the PPE). A seventy-ninth embodiment can include the method of the seventy-sixth to seventy-eight embodiments, further comprising transmitting, by the processor, a notice/warning indicative of end of service life (e.g. to a visual or audible warning device, which might be a handheld device with a screen and/or speaker, for example). An eightieth embodiment can include the method of the seventy-sixth to seventy-ninth embodiments, wherein retrieving the initial MFS comprises scanning/receiving from the wireless communication element (which stores the initial MFS) the initial MFS for the PPE and/or scanning the identifier element of the PPE (such as a bar code affixed to the PPE and linking the PPE to the initial MFS data stored elsewhere and accessible, for example wirelessly via the cloud) and retrieving the initial MFS from storage/memory. An eighty-first embodiment can include the method of the seventy-sixth to eightieth embodiments, further comprising, by the processor, determining which zone(s) of the PPE comprises (excessive) wear (e.g. determining one or more locations of (excessive) wear). An eighty-second embodiment can include the method of the seventy-sixth to eighty-first embodiments, further comprising fixing/repairing the one or more locations/zones of wear (e.g. in such a way as to restore the PPE service lite so that it operable to be put back into use in the field). An eighty-third embodiment can include the method of the seventy-sixth to eighty-second embodiments, further comprising retesting the repaired PPE, via the test rig, to determine that the repair has been successful. An eighty-fourth embodiment can include the method of the seventy-sixth to eighty-third embodiments, further comprising saving/storing the current MFS (e.g. into storage/memory linked/associated with the PPE, for example via the identifier element) (and wherein after a repair has taken place, updating the initial MFS and/or using the repaired MFS instead of the initial MFS going forward for testing/comparison, at least for that repaired zone of the PPE). An eighty-fifth embodiment can include the method of the seventy-sixth to eighty-fourth embodiments, wherein the test rig is portable/mobile (e.g. allowing testing in the field) (e.g. further wherein the placing the PPE into the test rig and determining the current MFS occurs in the field in proximity to the user's place of work). An eighty-sixth embodiment can include the method of the seventy-sixth to eighty-fifth embodiments, further comprising periodic re-testing of the PPE MFS to evaluate service life of the PPE (e.g. re-testing the PPE using the test rig as described above periodically (e.g. according to a pre-set schedule), for example, once per use/shift (such as before or after every use/shift), once per week, once per month, based on a percentage of the expected service life (for example, at the midpoint of the expected service life of the PPE and/or at ¾ of the expected service life), etc.). An eighty-seventh embodiment can include the method of the seventy-sixth to eighty-sixth embodiments, further comprising removing/retiring the PPE from use responsive to evaluation/determination that PPE has reached the end of its service life (which may account for safety factor—e.g. retire before end of safety factor, so before actual ultimate end of service life).

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support, for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An end of service life determination (ESLD) system comprising:
   a personal protective equipment (PPE);
   a processor of a handheld device of a user; and
   a test rig configured to communicate with the processor of the handheld device;
   wherein:
   the test rig further comprises one or more magnetic sensors;
   the PPE further comprises:
   magnetic particles;
   an identifier element or a wireless communication element;
   wherein:
   the magnetic particles are incorporated within or attached to the PPE; and
   the identifier element or the wireless communication element is attached to the PPE; and
   the processor is configured to receive a current magnetic field signature (MFS) sensor data of the PPE from the test rig and compare the current MFS sensor data with initial MFS associated with the PPE to determine whether the PPE has reached its end of service life, wherein the initial MFS is measured by the test rig.

2. The ESLD system of claim 1, wherein the initial MFS of the PPE is determined before use of the PPE, wherein the comparison by the processor of the received MFS sensor data to the initial MFS sensor data determines end of service life for the PPE, and wherein an amount of change in the MFS of the PPE is indicative of wear of the PPE.

3. The ESLD system of claim 1, wherein the wireless communication element comprises memory to store MFS information of the PPE, and wherein the identifier element is configured to uniquely identify the PPE.

4. The ESLD system of claim 1, wherein the handheld device is configured to interact with the wireless communication element or the identifier element to retrieve initial MFS sensor data corresponding with the PPE.

5. The ESLD system of claim 1, wherein the test rig comprises a plurality of sensors configured to measure the Gauss level, wherein the plurality of sensors corresponds to a respective test rig zone, and wherein the plurality of sensors are configured to determine the MFS of the PPE based on the test rig zone in which the corresponding plurality of sensors are placed.

6. The ESLD system of claim 5, wherein the test rig further comprises a mannequin element, wherein the PPE is placed on the mannequin element during testing, and wherein the mannequin element has a fixed orientation with respect to the magnetic sensors.

7. The ESLD system of claim 1, wherein the magnetic particles are distributed in a matrix of a material of the PPE.

8. The ESLD system of claim 1, wherein the magnetic particles are incorporated within the PPE by being blended into a polymeric compound or rubber.

9. The ESLD system of claim 5, wherein the test rig is portable.

10. A method of forming a personal protective equipment (PPE) with an initial magnetic field signature (MFS), comprising:
    blending magnetic particles into a polymeric compound;
    incorporating the polymeric compound with magnetic particles into the PPE, the PPE comprising an identifier element or a wireless communication element;
    placing the PPE into a test rig, wherein the test rig comprises one or more magnetic sensors; and
    determining, via the test rig, the initial MFS of the PPE, wherein the test rig is configured to transmit the initial MFS of the PPE to a processor of a handheld device for storage.

11. The method of claim 10, wherein incorporating the polymeric compound with magnetic particles into the PPE comprises one of the following:
    forming the polymeric compound into thread and sewing the thread into the PPE or adding the thread to the weave of the material used to form the PPE or sewing the thread onto a patch and affixing the patch onto the PPE;
    forming a coating material of the polymeric compound with magnetic particles and coating the PPE with the coating material;
    dipping a mold of the PPE into a liquid of the polymeric compound with magnetic particles to form the PPE;
    adding molten polymeric compound with magnetic particles into a mold for the PPE;
    mixing magnetic particles into the polymeric compound from which the PPE is to be formed;
    extruding a sheet of material from molten polymeric compound with magnetic particles distributed throughout; or
    combinations thereof.

12. A method of determining an end of service life for a personal protective equipment (PPE), the method comprising:
    retrieving, by a processor of a handheld device, an initial magnetic field signature (MFS) for magnetic particles within the PPE, wherein the PPE comprises an identifier element or a wireless communication element;
    placing the PPE into a test rig, wherein the test rig comprises one or more magnetic sensors;
    determining, by the test rig, the current MFS of the PPE;
    receiving, by the processor, the current MFS from the test rig; and
    evaluating, by the processor, a service life of the PPE or determining, by the processor, whether the PPE has reached its end of service life.

13. A personal protective equipment (PPE) device comprising:
    magnetic particles; and
    an identifier element or a wireless communication element;
    wherein:
    the magnetic particles are incorporated within or attached to the PPE; and
    the identifier element or the wireless communication element is attached to the PPE, wherein the PPE has a magnetic field signature (MFS) for the magnetic particles, and wherein an end of service life of the PPE is determined based on the MFS.

14. The PPE device of claim 13, wherein the magnetic particles are incorporated within the PPE by being blended into a polymeric compound or rubber.

15. The ESLD system of claim 1, wherein an alert is given within a safety factor when comparison of MFS indicates wear of the PPE.

16. The ESLD system of claim 1, wherein a pre-set amount of change of the MFS is indicative of end of service life for the PPE.

17. The method of claim 12, wherein blending the magnetic particles into the polymeric compound comprises distributing the magnetic particles substantially homogeneously throughout the polymeric compound.

18. The method of claim 12, wherein evaluating/determining service life of PPE comprises using the comparison of the current MFS of the PPE to the initial MFS of the PPE and the end of service life profile to evaluate life of the PPE.

19. The PPE device of claim 13, wherein the wireless communication element comprises memory/storage to store MFS information of the PPE, and wherein the identifier element is configured to uniquely identify the PPE.

* * * * *